United States Patent [19]

Rabenecker

[11] Patent Number: 5,139,746
[45] Date of Patent: Aug. 18, 1992

[54] MULTIPLE TEST TUBE HOLDER

[75] Inventor: Horst Rabenecker, Klein Parin, Fed. Rep. of Germany

[73] Assignee: Drägerwerk Aktiengesellschaft, Lübeck, Fed. Rep. of Germany

[21] Appl. No.: 449,531

[22] Filed: Dec. 11, 1989

[30] Foreign Application Priority Data

Dec. 28, 1988 [DE] Fed. Rep. of Germany ..... 38440970

[51] Int. Cl.⁵ ............................................. G01N 1/22
[52] U.S. Cl. ..................................... 422/104; 422/86;
422/88; 422/59; 211/71; 211/74; 211/80; 211/85
[58] Field of Search ............... 422/104, 86, 88, 59, 422/300, 310; 211/71, 74, 80, 85

[56] References Cited

U.S. PATENT DOCUMENTS

| 4,159,304 | 6/1979 | Shono | 422/104 |
| 4,389,372 | 6/1983 | Lalin | 422/88 |
| 4,923,806 | 5/1990 | Klodowski | 436/39 |
| 4,929,427 | 5/1990 | Guala | 422/100 |

FOREIGN PATENT DOCUMENTS 1386891 4/1988 U.S.S.R. .............................. 422/86

*Primary Examiner*—Lynn M. Kummert
*Attorney, Agent, or Firm*—McGlew & Tuttle

[57] ABSTRACT

The present invention pertains to a multiple holder for test tubes, which receives a plurality of individual test tubes for the simultaneous flow-through of a gas sample with the gas entering the tubes through at least one opened end, from a connection piece which has a flow outlet. The multiple holder of the invention receives commercially available test tubes with fused tips and includes an arrangement to simultaneously open all the test tubes introduced. To achieve this, the multiple holder 1 is designed such that at least one section 6, 6a can be tilted down, as a result of which the tips 8 of all the test tubes 2 introduced can be broken off simultaneously at least at one end.

15 Claims, 2 Drawing Sheets

MULTIPLE TEST TUBE HOLDER

FIELD OF THE INVENTION

The present invention pertains to a multiple holder for test tubes which receives a plurality of individual tubes for simultaneous flow-through of a gas sample. At least one end of the tubes are open, and the holder includes a connection piece that has a flow outlet.

BACKGROUND OF THE INVENTION

Such a multiple holder has become known from U.S. Pat. No. 4,040,783.

In the prior-art holder, a plurality of test tubes are held in a housing at their respective ends by a holding member which is designed as a plastic disk and is provided with passage openings, through which said test tubes pass. Each opening ends at a receiving device for the test tube. The receiving device is designed in the form of conical recesses around the passage openings. The housing has a bottom with an inlet opening for a gas sample and a cover with a corresponding outlet opening. A gas sample of varying composition is delivered by appropriate delivery means, e.g., a pump, through the test tubes being held between the bottom and the cover. The prior-art multiple holder is used, e.g., to detect the different components of an exhaust gas-air mixture. To do so, test tubes containing different detection reagents are placed into the holder.

The use of the prior-art multiple holder is associated with the disadvantage that the test tubes must be broken or opened at both ends before they are placed in the multiple holder. If, for example, the used test tubes are removed or new test tubes are introduced while the delivery pump continues to operate, the test tube removed last or the new test tube introduced first will be exposed to the stream of gas to be tested for the longest time, whereas the others are exposed to the gas to be tested for different detection times. This can be avoided in the prior-art multiple holder only by stopping the delivery pump to replace the test tubes. However, even in this case test tubes must already be opened and be placed as new tubes into the holder at all times. Foreign or harmful substances may penetrate into the filling of the opened test tubes during this handling and thus they may falsify the test reading during the subsequent analysis of the gas sample.

A measuring arrangement for exhaust gas testing, in which a plurality of test tubes arranged in parallel to one another and branch off from an exhaust gas line, is described in West German Auslegungsschrift No. 21,51,435. The tubes are connected to a pump unit which delivers the exhaust gas sample through the test tubes. When test tubes are introduced, each test tube must be connected to the pump unit in the opened state one by one in the case of this measuring device as well, which leads to different flow-through times of the gas to be tested for each test tube.

In the multiple holder according to West German Patent Specification No. 36,37,869, test tubes equipped with diaphragm closures at their ends are used. A plurality of test tubes are received by one crosspiece. All diaphragm closures of the test tubes introduced are opened simultaneously on joining a connection piece. The test tubes are connected to the delivery pump via the connection piece.

Even though the above-described disadvantages are avoided in this West German Patent 36,37,869, it is not possible to use commercially available test tubes. The test tubes with diaphragm closures must be manufactured specially, and they have the additional disadvantage that they are not sealed as tightly as the test tubes with fused tips and ar damaged more readily.

SUMMARY AND OBJECT OF THE INVENTION

It is an object of the present invention to improve a multiple test tube holder, with which all the test tubes introduced can be prepared simultaneously for the analysis of a gas sample and to enable it to receive commercially available test tubes with fused tips. The test tubes introduced shall be able to be opened simultaneously without any additional aids. To achieve this task, at least one section of the multiple holder can be tilted down, as a result of which the tips of all the test tubes introduced can be broken off at least at one end. Opening at one end only is used in the case of diffusion tubes.

The advantages achieved with the present invention are that the necessary number and type of the closed, commercially available test tubes can be accommodated in the holder. An attached connection piece establishes the common connection to a delivery pump. When sampling is to be started, all the test tubes introduced can be opened simultaneously by means of the multiple holder. To break off the tips, the test tubes are either scored beforehand, or an appropriate area of the tips is provided with a predetermined breaking point. Subsequently, they can be exposed to the ga to be tested simultaneously.

The closing bars cover the tips of the test tubes and thus protect them from being broken off unintentionally. A holder provided with test tubes forms a compact unit, which can be packed easily and safely.

The use of the closing bar as a striking bar to score the test tubes guarantees uniform scoring of the test tubes in a simple manner, and the breaking point is located in the same area in all test tubes, namely, where the breaking force is applied during the tilting of the closing bar. This guarantees reliable opening of the test tubes with a weak force.

It is also advantageous that the tips broken off remain in the closing bar and can be disposed of together with same. Consequently, there is no risk of injury by glass splinters.

The flexible film connections, by which the closing bars are attached to the multiple holder, may also be made stretchable by making them, e.g., of an elastic material, such as rubber.

This makes it possible to introduce the test tubes into the multiple holder in a simple manner. The test tubes are first introduced into the multiple holder with the closing bars in the tilted-down position, and the closing bars are subsequently pulled over the tips of the test tubes while the length of the flexible film connections increases due to stretching. The flexible film connections will subsequently pull the closing bars toward the tips of the test tubes and provide for their safe holding in the multiple holder.

The various features of novelty which characterize the invention are pointed out with particularity in the claims annexed to and forming a part of this disclosure. For a better understanding of the invention, its operating advantages and specific objects obtained by its uses, reference is made to the accompanying drawings an descriptive matter in which preferred embodiments of the invention are illustrated.

DETAILED DESCRIPTION OF THE PREFERRED EMBODIMENTS

Figure 1:
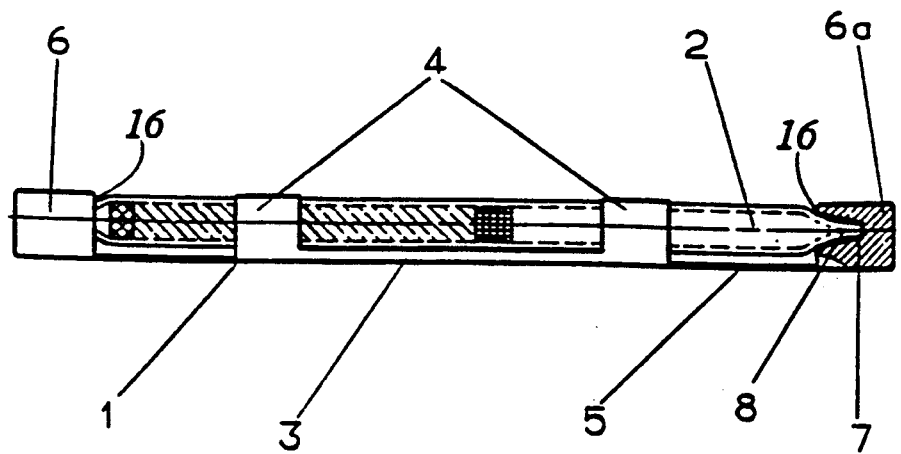
FIG. 1 is a side view of a multiple holder made in one piece.
Figure 2:
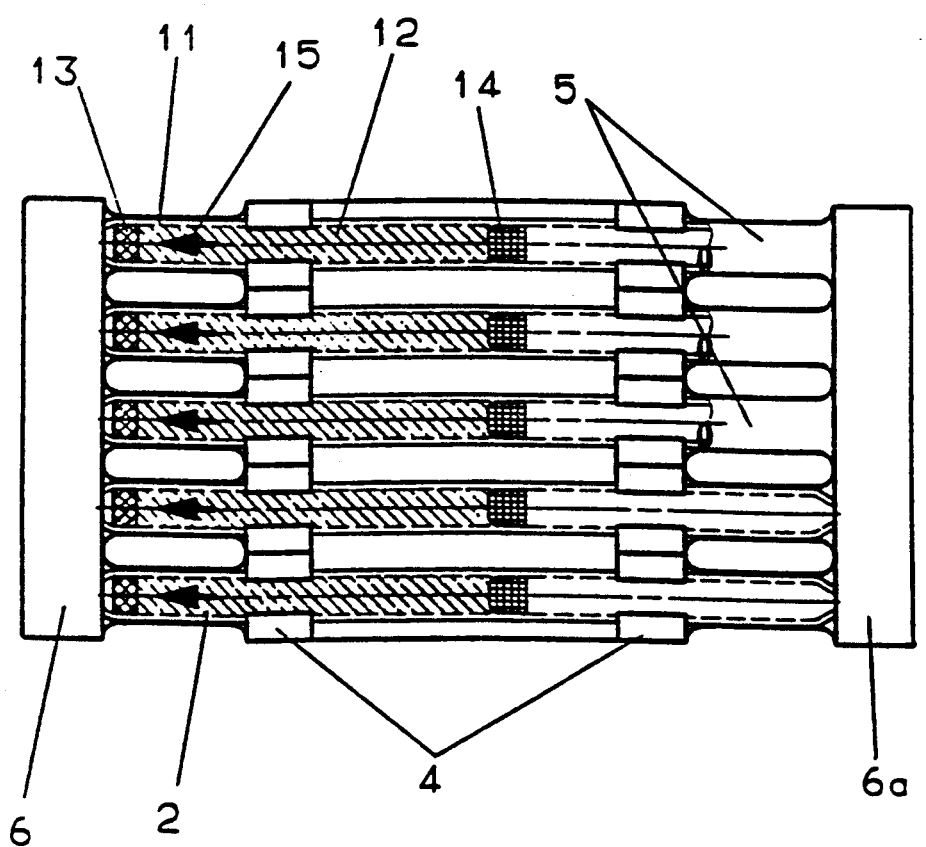
FIG. 2 is a top view of the same multiple holder of FIG. 1.

FIGS. 1 and 2 show a multiple holder 1 made in one piece for five test tubes 2.

A plate 3 is provided with holding clamps 4 to fix the test tubes. Via bands 5 serving as the film connection, the plate 3 is connected to the closing bars 6, 6a, which are provided with holes 7 that reach over the fused tips 8 of the test tubes. Consequently, the test tubes are held in this multiple holder by the holding clamps 4 and, by their tips, by the closing bars 6, 6a. To place the test tubes into the multiple holder, the closing bars 6, 6a are snapped over the tips 8 of the test tubes while the bands 5 stretch longitudinally. To make longitudinal stretching possible without problems, the multiple holder is made of an elastomer of appropriate stretching ability.

To use this test tube set, the tips are first scored on one side with an appropriate tool such as an ampule file or a corner 16 of the connection closing bar 6 can be used as a striking edge. The scored tips can be broken off simultaneously by tilting the closing plate down. The test tubes are now open on one side.

Figure 4:
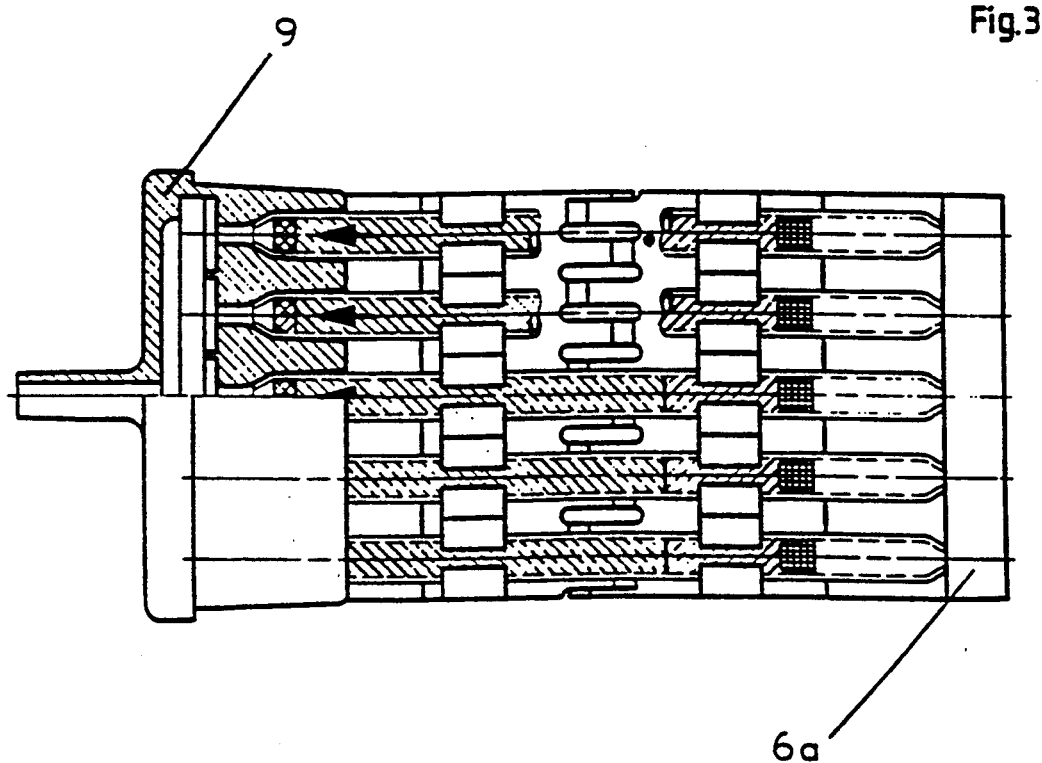
FIG. 4 is a top view of the multiple holder of FIG. 3 with the connection piece in place.

The opened ends of the test tubes are placed into the connection piece 9 shown in FIG. 4, and closing bar 6a, which covers the test tube tips that have not been opened as yet, serves as an aid when pressing the test tubes into the connection piece and offers protection against injuries. The still closed tips of the test tubes are subsequently scored, and then broken off by tilting down said closing bar 6a. The test tubes are now open at both ends, and flow is thus able to take place through them.

Figure 3:
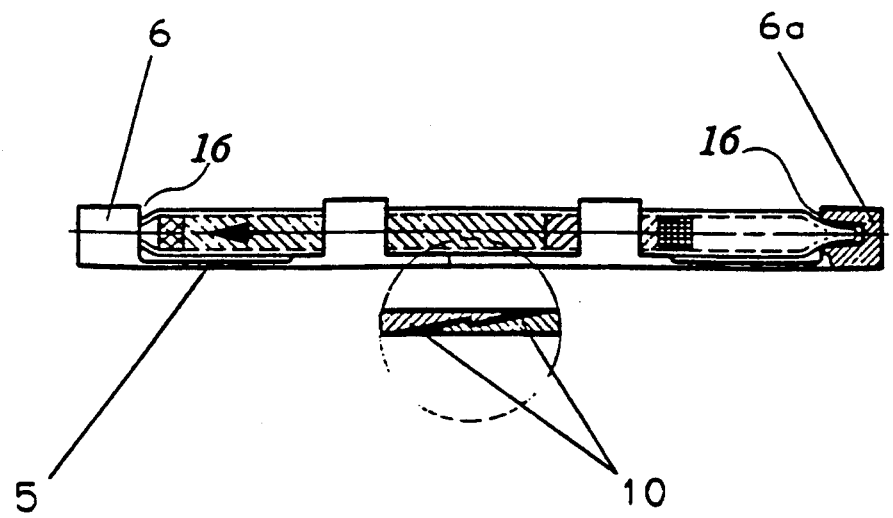
FIG. 3 is a side view of a two-part multiple holder of a second embodiment of the invention.

In another embodiment (FIGS. 3 and 4), the holder is made of two parts and is manufactured from a thermoplastic material. The two halves are identical and are pushed together after introducing the test tubes. The snap fasteners 10, which are arranged in a staggered pattern, penetrate into one another and hold the two individual parts together.

The bands 5 are so thin that the closing bars 6 and 6a can be tilted down without any problem to open the test tubes.

The inner design of the test tubes shown will be briefly described on the basis of FIG. 2.

An indicator mass 12 is arranged between two holding members 13, 14 inside a glass tube 11. A printed arrow 15 indicates the intended direction of flow. On contact with the gas which the test tube is intended to detect, the indicator mass shows a characteristic change in color. The quantity of the gas detected can be inferred from the length of the zone showing the change in color.

Such standard gas indicating test tubes may be positioned in the multiple holder one, as discussed above, by inserting each test tube with scored tip in a closing bar 6 and then snapping the other closing bar 6a over the tips at the other end (scored if necessary) with the help of longitudinal stretching. The braking of the tips is accomplished as discussed above by merely tilting down one of the closing bars 6, 6a depending upon the tips which are to be broken. While the closing bars are tilted down, the connection piece 9 may be connected over the opened ends. Inserting the test tubes is simplified by the embodiment of FIG. 3 in which two different portions of the assembly may be connected at connection 10, thereby eliminating any difficulties in placing the tubes in the multiple holder 1.

While specific embodiments of the invention have been shown and described in detail to illustrate the application of the principles of the invention, it will be understood that the invention may be embodied otherwise without departing from such principles.

What is claimed is:

1. A multiple test tube holder arrangement for arranging test tubes for flow-through gas sampling, comprising: a flat and rigid test tube holder body portion, for receiving a plurality of test tubes; test tube tip engaging means for receiving a test tube tip of each test tube positioned in said holder body portion; and flat flexible band means connected to said holder body portion and connected to said test tube tip engaging means for tilting said test tube tip engaging means relative to said holder body portion for breaking each of a plurality of test tube tips while maintaining the test tubes in said holder body portion.

2. A multiple test tube holder arrangement according to claim 1, further comprising additional tip engaging means connected to a second end of said flat and rigid holder body portion, said flat and rigid holder body portion having snap fastening means including first and second connectible body elements, allowing tips of each of the plurality of test tubes to be engaged by said tip engaging means and subsequent connection of said flat and rigid holder body portion.

3. A multiple test tube holder arrangement according to claim 1, further comprising: a multiple test tube connection piece for connecting open ends of the plurality of held test tubes upon tilting said tip engaging means to expose an open end of each of the test tubes.

4. A test tube holder for removing a tip from a test tube, the holder comprising:

a plate;

holding clamp means attached to said plate for securely holding a test tube to said plate, said holding clamp means only contacting a portion of the test tube leaving a portion exposed for displaying contents of the test tube; and tilting means connected to said plate for receiving the tip of the test tube and for tilting the tip relative to the held test tube to break off the tip from the test tube.

5. A holder in accordance with claim 4, wherein: said plate is flat and rigid.

6. A holder in accordance with claim 4, wherein: said tilting means has a flexible band means attached on a first end to said plate, said tilting means also has a closing bar attached to a second end of said flexible band means, said closing bar defining a tip receiving portion for receiving the tip of the test tube, and said closing bar being tiltable with respect to said plate by said flexible band means for breaking off the tip of the test tube.

7. A multiple test tube holder according to claim 6, wherein said closing bar includes a striking edges for scoring said test tubes.

8. A holder in accordance with claim 6, wherein:
said flexible band means is stretchable to an extent that said closing bar contacts the tip of the test tube in holding position, and said closing bar can be stretched away from the tip of the test tube for insertion or removal of the test tube.

9. A holder in accordance with claim 6, further comprising:
snap fastener means between said holding clamp means and said closing bar for separating and connecting said holding clamp means to said closing bar, the test tube being insertable into the holding clamp means during separating by said snap fastener means, and said closing bar being brought into contact with the tip of the test tube during connecting by the snap fastener means.

10. A holder in accordance with claim 6, wherein:
said flexible band means is flat.

11. A holder in accordance with claim 4, further comprising:
an additional tilting means connected to another end of said plate for receiving another tip of the test tube and for tilting the tip relative to the held test tube, to break off the another tip of the test tube.

12. A holder in accordance with claim 4, wherein:
said holding clamp means has two fingers protruding from said plate and the test tube is clamped between said two fingers.

13. A holder in accordance with claim 12, wherein:
said holding clamp means has an additional two fingers protruding from said plate and the test the is clamped between said two fingers and is also clamped between said additional two fingers.

14. A holder in accordance with claim 13, further comprising:
snap fastener means between said two fingers and said additional two fingers for separating and connecting said two fingers to said additional two fingers, the test tube being insertable into the holding clamp means during separating by said snap fastener means, and said closing bar being brought into contact with the tip of the test tube during connecting by the snap fastener means.

15. A holder in accordance with claim 4, wherein:
said holding clamp means holding a plurality of test tubes; and
said tilting means receiving a plurality of tips of test tubes for tilting the plurality of tips relative to the held plurality of test tubes to break off the plurality of tips from the plurality of test tubes.

* * * * *